United States Patent [19]

Franetzki et al.

[11] 4,122,839

[45] Oct. 31, 1978

[54] APPARATUS FOR THE DETERMINATION OF RESPIRATORY PASSAGEWAY RESISTANCE

[75] Inventors: Manfred Franetzki, Erlangen; Volker Korn, Nurnberg; Karl Prestele, Erlangen, all of Germany

[73] Assignee: Siemens Aktiengesellschaft, Berlin & Munich, Germany

[21] Appl. No.: 762,952

[22] Filed: Jan. 26, 1977

Related U.S. Application Data

[63] Continuation-in-part of Ser. No. 559,655, Mar. 18, 1975, Pat. No. 4,022,193.

[30] Foreign Application Priority Data

Mar. 22, 1974 [DE] Fed. Rep. of Germany ....... 2413960
Nov. 28, 1974 [FR] France ................................ 74 38991

[51] Int. Cl.² .............................................. A61B 5/08
[52] U.S. Cl. ...................................... 128/2.08; 73/211
[58] Field of Search ................... 128/2.08, 2.07, 2 C, 128/DIG. 25; 73/211

[56] References Cited

U.S. PATENT DOCUMENTS

| | | | |
|---|---|---|---|
| 3,036,569 | 5/1962 | Clement et al. | 128/2.08 |
| 3,598,111 | 8/1971 | Kahn et al. | 128/2.08 |
| 3,621,833 | 11/1971 | Crane | 128/2.08 |
| 3,713,436 | 1/1973 | Hardway, Jr. | 128/2.08 |
| 3,726,271 | 4/1973 | Mondshine et al. | 128/2.08 |
| 3,857,385 | 12/1974 | Hampl | 128/2.08 |

FOREIGN PATENT DOCUMENTS

| | | | |
|---|---|---|---|
| 2,044,101 | 9/1972 | Fed. Rep. of Germany | 128/2.08 |
| 2,233,829 | 3/1974 | Fed. Rep. of Germany | 128/2.08 |
| 850,750 | 10/1960 | United Kingdom | 128/2.08 |

*Primary Examiner*—Lee S. Cohen
*Attorney, Agent, or Firm*—Hill, Gross, Simpson, Van Santen, Steadman, Chiara & Simpson

[57] ABSTRACT

An apparatus for the determination of the respiratory passageways resistance, including a flow resistance in the breathing or respiratory flow passageway, whose resistance value is periodically varied by a frequency which lies above the breathing frequency, and including as well a pressure and/or, as occasioned, a flow measurement gauge. In conjunction with the flow resistance, the resistance value thereof is varied in an essential sinusoidal manner, and the pressure and/or flow measurement gauge incorporates two measuring passageways, there being detected in the first passageway only the pressure and/or occasioned flow components in the respiratory passageway due to the lower frequencied breathing, and in the second passageway the higher frequencied resistance variations.

1 Claim, 3 Drawing Figures

APPARATUS FOR THE DETERMINATION OF RESPIRATORY PASSAGEWAY RESISTANCE

CROSS-REFERENCE TO RELATED APPLICATION

The present application is a continuation-in-part of the parent application Ser. No. 559,655 filed Mar. 18, 1975, now U.S. Pat. No. 4,022,193 dated May 10, 1977.

BACKGROUND OF THE INVENTION

1. Field of the Invention

The present invention relates to an apparatus for the determination of the respiratory passageways resistance, including a flow resistance in the breathing or respiratory flow passageway, whose resistance value is periodically varied by means of a frequency which lies above the breathing frequency, and including as well a pressure and/or, as occasioned, a flow measurement gauge.

2. Discussion of the Prior Art

In known apparatus of this type (for example German Published Specification No. 1,029,526, in addition to the therein referred state of the art) there are provided two flow resistance in the respiratory passageway, of which one (auxiliary resistance) may be periodically suddenly connected to the other by means of a valve or shutter, and again disconnected therefrom. In the periodic square-wave shaped variation of the flow resistance, there may then be measured for one the pressure drop $p_z$ thereacross at the obtained total resistance W at a therewith connected auxiliary resistance, and for the other the pressure drop $p_o$ thereacross at the obtained residual resistance $W_2$ at a disconnected auxiliary resistance. From the resistance W and $W_2$, as well as the measured differential pressures $p_z$, respectively $p_o$, there is then calculated the respiratory flow resistance $W_i$ pursuant to the relationship $$W_i = \frac{W_2 \cdot W \cdot (p_z - p_o)}{p_o \cdot W_2 - p_z \cdot W}.$$

The respiratory passageway resistances which are obtained in accordance with the known measuring principles, however, are not sufficiently exact.

SUMMARY OF THE INVENTION

Accordingly, it is an object of the present invention to provide an apparatus of the above-mentioned type in which the respiratory passageway resistance may be obtained in a substantially more exact manner.

The foregoing object is inventively achieved in that means are associated with the flow resistance, which preferably vary the resistance value thereof in an essential sinusoidal manner, and wherein the pressure and/or flow measurement gauge incorporates two measuring passageways, there being detected in the first passageway only the pressure and/or occasioned flow components in the respiratory passageway due the lower frequencied breathing, and in the second passageway the higher frequencied resistance variations.

The invention follows investigations in which the usual measuring principles did not deliver sufficiently exact measurement results. As the first essential reason therefore it has been found that the known measuring principles do not detect, as is inherently required, the respiratory passageway resistance as an actual component of an alternating or variable flow respiratory passageway impedance separately from capacitive and/or inductive resistance components (which play a not insignificant role due to the resistance variations caused, relatively high frequencied pressure and/or flow variations in the respiratory passageway).

More frequently there is always obtained as the "respiratory passageway resistance" a conglomerate of two resistance components. A second reason for measurement errors possibly lies in that the resistance changes are periodically encountered in a sudden manner. These sudden resistance changes correspondingly lead to sudden pressure or flow variations in the respiratory flow passageway which, on the one hand, cause vibrations of, for example, the cheeks or other soft portions of the mouth or trachea and thereby may cause signal deformations, or distortions. Hereby it is also possible that short-circuit capacitances may come into effect. On the other hand, experience has shown that the probed person reacts physically and psychically to those types of sudden pressure or flow variations, and consequently breathes unnaturally.

In the apparatus according to the present invention, the flow resistance preferably is varied essentially sinusoidally. By means of the thus smoothed oscillations there is created very little danger that the mouth or tracheal portions of the person being probed will vibrate therewith, or that the patient will react unnaturally to these vibrations. If these advantages of an essentially sinusoidal resistance variation (being merely preferably utilized) are viewed as unimportant, then the resistance variation or charge may also be carried out, as known, in a square-wave form, or otherwise. The only care which must then be taken is that by means of the pressure and/or current measuring gauge in the particular passageway, the respective basic wave of the alternating pressure and/or the alternating flow must be detected. The square-wave shaped or otherwise formed resistance variation should then fall within the scope of the present invention. A much more important advantage is however provided in that, for the selected resistance variation, the "complex" respiratory passageway resistance now may be exactly divided into the inherent actual component an alternating flow resistance, and into the imaginary component formed of capacitive and/or inductive portions.

If the flow resistance is separated into a constant basic portion $R_o$ and into the alternating portion $r$ (basic wave), then there is obtained for the entire external resistance the time-wise varying value $R = R_o + r$. Correspondingly, there is then obtained for the flow V, as well for the pressure $P_M$ in the breathing tube, the relationship: $V = V_o + v$ or, respectively, $P_M = P_{Mo} + p_M$. If the variable resistance component $r$ is selected to be extremely small, then the alternating components $v$, $p_M$ are also small.

In accordance with the relationship $P_M = V \cdot R = (V_o + v) \cdot (R_o + r)$, under consideration that the variations of the external resistance have no influence on the breathing (small amplitude) and that the external resistance is independent of the breathing (preferably attained by the introduction of a flow resistance as the basic resistance $R_o$ constructed pursuant to the principle of a lamellar receptor according to German Laid-Open Patent Specification No. 2,044,101), there is obtained the lower frequencied, meaning merely due to the breathing, pressure component for $P_{Mo} = V_o \cdot R_o$, and the higher frequencied, meaning the pressure component emanating from the resistance variations for $p_M = V_o r + R_o v$.

The component $P_M$ may then signify the terminal voltage of an alternating voltage source with the base voltage $p_E = V_o \cdot r = P_{Mo}/R_o \cdot r$ at the internal resistance $R_o$.

From this equivalent-circuit diagram there may then be obtained the complex alternating current-respiratory passageway resistance through $$-\dot{v} R_{aw} = p_M = \dot{v} R_o + p_E \text{zu } R_{aw} = -(R_o + \dot{V}_o \cdot r/\dot{v}) \quad 1$$

or $$R_{aw} = -R_o^2 \left( \frac{p_M}{R_o P_M - P_{Mo} r} \right). \quad 2$$

Converting in consideration of the sinusoidal resistance variations $r$ (basic wave) into the complex notation and setting $$r = \hat{r} e^{j\omega t} = a R_o e^{j\omega t}$$

$$\dot{v} = -\hat{v} e^{j(\bar{\omega} t + \alpha)} = -b \dot{V}_o e^{j(\omega t + \alpha)}$$

$$P_M = \hat{p}_M e^{j(\omega t + \beta)} = c P_{Mo} e^{j(\omega t + \beta)},$$

wherein $\omega$ is the basic frequency of the sine oscillations; $a$, $b$, $c$ are proportionality factors, and $\alpha$, respectively, $\beta$ represent phase angles, then from the above relationship 1 there is obtained $$R_{aw} = R_o (a/b \cdot e^{-j\alpha} - 1)$$

and from the above relationship 2 there is obtained $$R_{aw} = R_o \frac{1}{\frac{a}{c} e^{j\beta} - 1},$$

wherein $$a/b = \frac{\hat{r}}{R_o} \cdot \frac{\dot{V}_o}{\hat{v}} \text{ and } a/c = \frac{\hat{r}}{R_o} \cdot \frac{P_{Mo}}{\hat{p}_M}.$$

Under the assumption that the lung itself does not provide any additional component to the resistance, so that tissue viscosities do not play any role, and the lung at the most adds capacitively or inductively to the total impedance, then the actual component of these impedances represents the sought after passageway resistance. This actual component may however be easily determined, through the apparatus according to the invention separately detected, individual magnitudes $\hat{p}_M$, $P_{Mo}$ or, as occasioned, $\dot{V}_o$, $\hat{v}$, as well as from the known magnitudes $R_o$ and $\hat{r}$ ($R_o$ and $\hat{r}$ are predetermined through the particular flow resistance and the sine amplitudes of the resistance variations). Since, experience-wise the mouth pressure may be more phase-precisely ascertained than, for example, the breath flow, the mouth pressure measurement is suitably preferred to the flow measurement. From the last-indicated above-listed relationship, there is then obtained in a simple manner the actual component, for example, for an insignificantly small phase angle, for $$R_{aw} = R_o \frac{\hat{p}_M}{a \cdot P_{Mo} - \hat{p}_M}.$$

The magnitudes $\hat{p}_M$, $P_{Mo}$ (as occasioned, for current measurements, the magnitudes $\dot{V}_o$, $\hat{v}$), may be simply obtained in a preferred embodiment of the invention by means of a single mechanical-electrical transducer (for example, a flow transducer), which is connected into the respiratory passageway upstream of the flow resistance, and which each have an electrical frequency filter associated therewith, whereby the first frequency filter is destined for the determination of $P_{Mo}$ (respectively $\dot{V}_o$) on respiratory frequencies, and the second for the determination of $\hat{p}_M$ (respectively $\hat{v}$) at the sine frequency of the resistance variations. The calculation of the measured pressure magnitudes $P_{Mo}$ and $\hat{p}_M$ (respectively $\dot{V}_o$, $\hat{v}$) together with the known resistance magnitudes $R_o$ and $\hat{r}$ to the respiratory passageway resistance may be carried out, for example, by means of a slide rule or graphically. Preferably, however, there should be provided an electronic computer circuit, which includes correspondingly selected multiplier elements, divider elements, and differentiating formers for the automatic computation of the respiratory passageway resistance in accordance with the above relationships.

BRIEF DESCRIPTION OF THE DRAWINGS

Further advantages and details of the invention may now be ascertained from the following description of an embodiment of an apparatus equipped for pressure measurement, taken in conjunction with the accompanying drawing; in which.

DETAILED DESCRIPTION

Figure 1:
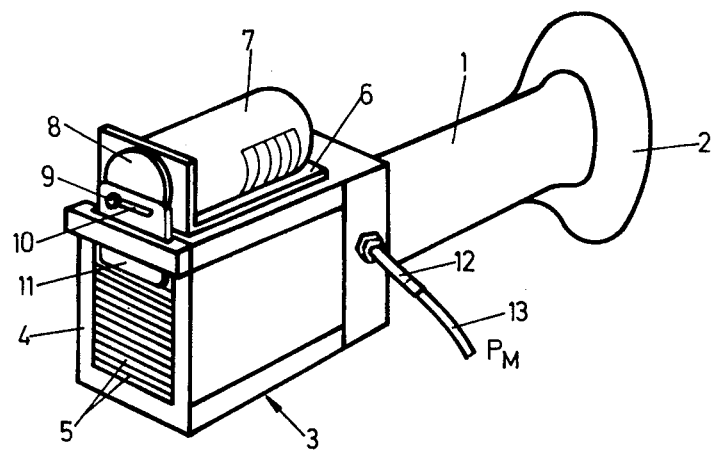
FIG. 1 perspectively illustrates the mechanical construction of an apparatus constructed pursuant to the present invention.

Referring to FIG. 1, a breathing tube is designated by reference numeral 1, whose mouth-sided end includes a sealable mouth applicator 2 which is formed, for example, of rubber or the like, whose other end is closed off with a type of lamellar receptor 3 constituting a basic flow resistance. The lamellar receptor 3 (generally corresponding to the lamellar receptor disclosed in German Laid-Open Patent Specification No. 2,044,101) consists of a housing 4, whose inner chamber is divided into a plurality of narrow (approximately 0.2 mm wide) parallel flow chambers by means of thin foils 5 which are formed, for example, of polyvinyl chloride. The flow receiving surface of the receptor 3 is selected of a size so that the basic resistance value of the flow resistance preferably lies within the range of 1 to 5 mbar/1/s.

An electromotor 7 is mounted on the cover of the lamellar receptor 3 by means of an elbow or angle section 6. This motor, in its operative condition, places a disc 8 into rotation. The disc 8, in turn, is in communication with a shutter plate 11 through the intermediary of an eccentric shaft guide component 9, as well as guide slot 10. Upon rotation by the motor shaft, and thereby disc 8, this shutter plate 11 is periodically articulated across a portion of the flow surface of the lamellar receptor 3, and thereby serves as an element for subjecting the basic resistance value $R_o$ of the lamellar receptor 3 to periodic resistance variations $r$. The guide 9, 10 between disc 8 and the shutter plate 11 is so constructed that the linear articulation of the plate 11 across the flow surface of the receptor 3 essentially is carried out in a sinusoidal manner, so that thereby are obtained also correspondingly sinusoidal resistance variations. The lift or height of the sine variations thereby should consist of a maximum $r = \pm 10\%$ of the basic flow resistance $R_o$, meaning for example, at 5 mbar/1/s a maximum of $\pm 0.5$ mbar/1/s. Selected as the sine frequency should be frequencies in the range of between approximately 3 to 20 Hz, and preferably 12 Hz.

In the apparatus constructed pursuant to FIG. 1, in the operative condition thereof (the patient breathes with the shutter plate 11 moving, into the mouthpiece 2 and through the breathing tube 1 and receptor 3), the total mouth pressure $P_M$ is read off through a single pressure outlet connector 12 having a pneumatic connector conduit 13 which connects in at a connecting location between breathing tube 1 and the lamellar receptor 3.

Figure 2:
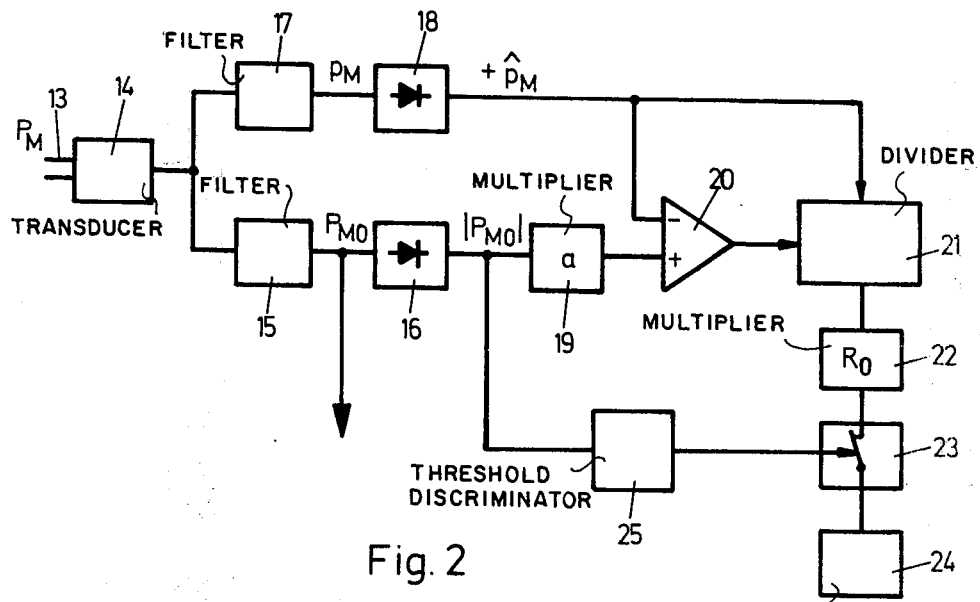
FIG. 2 illustrates an associated electrically measuring and calculating circuit for the apparatus in diagrammatic representation.

This pressure $P_M$, according to FIG. 2, is transmitted to a mechanical-electrical transducer 14. From the herein generated electrical pressure signals there is then ascertained in a first measuring passageway, the latter of which includes a low-pass filter 15 with a limiting frequency of approximately 4 Hz, as well as a following rectifier 16, the lower frequencied pressure components $P_{Mo}$ due merely to breathing. Correspondingly, in a second measuring passageway, which includes a band-pass filter 17 with a following rectifier 18, and which is set to the sine frequency of the resistance variations, for example 12 Hz, there are obtained the pressure change components $\hat{p}_M$ which emanate from the higher frequencied sinusoidal resistance variations.

The thus obtained components $P_{Mo}$, $\hat{p}_M$ are then transmitted to an electrical computer circuit for the computational ascertaining of the respiratory passageway resistance $R_{aw}$. This calculating or computer circuit consists in detail of a first multiplier element 19 (proportionality element such as, for example, a resistance potentiometer) which multiplies the measured magnitude $P_M$ by the factor $a = \hat{r}/R_o$, a differential former 20 (operational amplifier) for the formation of the differential signal $\hat{r}/R_o \cdot P_{Mo} - \hat{p}_M$, a divider element 21 for calculation of the quotient $$\frac{\hat{p}_M}{\frac{\hat{r}}{R_o} \cdot P_{Mo} - \hat{p}_M},$$

as well as a second multipler element 22 for the multiplication of the quotient signal with the constant factor $R_o$ (basic resistance value).

At the output of the element 22 (output of the computer circuit) there thus appears a signal which corresponds to the sought after respiratory passageway resistance, in accordance with the relationship $$R_{aw} = R_o \frac{\hat{p}_M}{\frac{\hat{r}}{R_o} \cdot P_{Mo} - \hat{p}_M}.$$

Since the respiratory passageway resistance for diminishing breath flows (zero-through passage of the breath flow) is not defined ($R_{aw} \rightarrow o/o$), then an electrical breaker contact 23 is further provided between the output of the computer circuit and an indicating or registration apparatus 24 for the calculated respiratory passageway resistance $R_{aw}$. This breaker contact is then always opened, and thereby prevents a resistance indication, when the signal component $P_{Mo}$ at the output of the rectifier 16 falls below a predetermined lower threshold value. The actuation of the contact 23 is carried out through the output signal of a threshold discriminator 25 which is set at the threshold.

The respiratory passageway resistance $R_{aw}$ may be directly indicated on the indicating apparatus 24 as a resistance value. However, the possibility also exists that the resistance $R_{aw}$ may be recorded as a function of the breath flow $\dot{V}_o$. Hereby, read off between the low-pass filter 15 and the rectifier 16 is a signal $P_{Mo}$ which is proportional to the breath flow $\dot{V}_o$, and after suitable calibration (indicated by the arrow), transmitted as a current signal, together with the resistance signal $R_{aw}$, to a two-component recorder or the like for the joint recordation thereof.

In accordance with a further embodiment of the present invention, there is provided a flow tube in which the flow resistance varies periodically at a frequency lying above the breathing frequency. This flow resistance is in the form of a single fixed resistance 5 located on the flow tube 1, and has a flow surface determining a basic resistance value. A sinusoidally variable shutter 11 is associated with the flow surface of the single fixed resistance for the periodic and substantially sinusoidal superposition of resistance variations onto the basic resistance value $R_o$. A mechanical-electrical pressure transducer 14 is connected by conduit to the flow tube 1 and has two measurement passageways connected to the output of the transducer. Each passageway is provided with a frequency filter, and the frequency filter 15 in one passageway ascertains pressure components due to low frequency breathing. The frequency filter 17 in the other passageway ascertains pressure components due to higher frequency resistance variations caused by the shutter 11. One of electrical multiplying elements 19, 22 is connected to the output of the measurement passageway with the frequency filter 15. A difference element 20 is connected to the outputs of that multiplying element and the other passageway. A dividing element 21 is connected to the outputs of the other passageway with the filter 17 and of the difference element and a further multiplying element connected to the output of the dividing element. The elements or components are interconnected and adapted to mathematically provide the respiratory passageway resistance $R_{aw}$ from the lower and higher frequency flow components $\dot{V}_o$ and $\dot{v}$ obtained from the measurement passageways, and from the resistance values $R_o$ and $r$ in accordance with the relationship $$R_{aw} = R_o\left(\frac{r}{R_o} \cdot \frac{\dot{V}_o}{\dot{v}} - 1\right).$$

Figure 3:
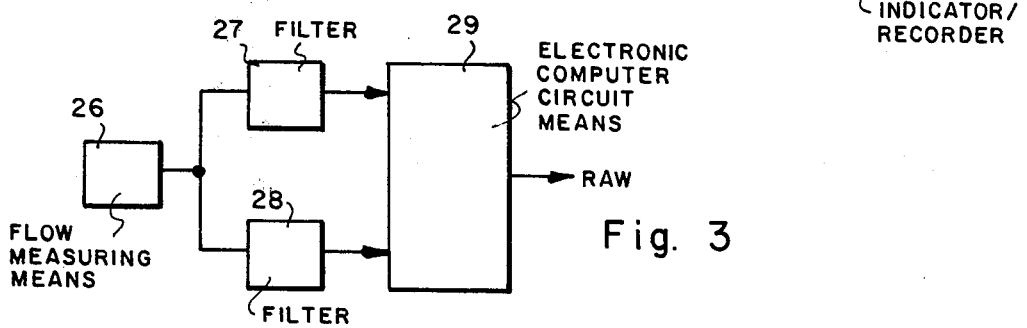
FIG. 3 shows circuitry for obtaining respiratory passageway resistance based on flow measurement and utilizing flow measuring means which is to be associated with apparatus of the type shown in FIG. 1.

FIG. 3 illustrates the alternative described in the Summary of the Invention wherein means are associated with the flow resistance, such as indicated at 7–11 in FIG. 1, which preferably vary the resistance value in an essentially sinusoidal manner, and wherein a flow measuring gauge incorporates two measuring passageways as shown in FIG. 3, there being detected in the first passageway only the flow components in the respiratory passageway due to the lower frequencied breathing, and in the second passageway the higher frequencied resistance variations.

If the flow resistance is separated into a constant basic portion $R_o$ and into the alternating portion $r$ (basic wave), then there is obtained for the entire external resistance the timewise varying value $R = R_o + r$. Correspondingly, there is then obtained for the flow $\dot{V}$ in the breathing tube 1, FIG. 1, the relationship: $\dot{V} = \dot{V}_o + \dot{v}$. If the variable resistance component $r$ is selected to be extremely small, then the alternating component $\dot{v}$ is also small.

As discussed in detail in the Summary of the Invention, the passageway resistance is easily determined, since the required flow magnitudes may be simply obtained by means of a single mechanical-electrical transducer, for example a flow transducer or flow measuring means as indicated at 26 in FIG. 3. The flow measuring means has a first frequency filter 27 and a second frequency filter 28 connected therewith and comprising the respective first and second measuring passageways of the flow measurement gauge of FIG. 3. The first frequency filter 27 is destined for the determination of $\dot{V}_o$, while the second filter 28 is for the determination of $\dot{v}$ at the sine frequency of the resistance variations. The calculation of respiratory passageway resistance from the measured flow magnitudes together with the known resistance magnitudes may be carried out, for example, by means of a slide rule or graphically. Preferably, however, there should be provided an electronic computer circuit means such as indicated at 29 in FIG. 3 which includes correspondingly selected multiplier elements, divider elements, and differentiating formers for the automatic computation of the respiratory passageway resistance in accordance with the relationship given in the Summary of the Invention, namely:

$$R_{aw} = R_o(a/b \cdot e^{-j\alpha} - 1)$$

where $$a/b = \frac{\hat{r}}{R_o} \cdot \frac{\dot{V}_o}{\hat{\dot{v}}}$$

and $\alpha$ represents a phase angle.

To summarize the embodiment of FIG. 3 with reference to the original claim terminology, the flow measuring means 26 is connected to the flow pipe. The first and second measurement passageways comprise respective first and second filters 27 and 28 connected to the output of the flow measuring means 26. The first frequency filter of filter component 27 ascertains flow component due to low frequency breathing, while the second frequency filter of the filter component 28 ascertains flow components due to the higher frequency resistance variations caused by the shutter 11, FIG. 1. Computer circuit means 29, as previously explained, may comprise multiplier means, divider means and difference forming means to provide the respiratory passageway resistance $R_{aw}$ from the lower and higher frequency flow components $\dot{V}_o$ and $\dot{v}$ obtained from the measurement passageways, and from the resistance values $R_o$ and $r$ in accordance with the relationship $$R_{aw} = R_o\left(\frac{r}{R_o} \cdot \frac{\dot{V}_o}{\dot{v}} - 1\right).$$

While there has been shown what is considered to be the preferred embodiment of the invention, it will be obvious that modifications may be made which come within the scope of the disclosure of the specification.

What is claimed is:

1. In an apparatus for determining respiratory passageway resistance, including a flow tube having a passageway including a flow resistance with means for varying the resistance value periodically at a frequency lying above the breathing frequency, measuring means for supplying a measurement signal which varies in accordance with a parameter of the flow in the flow tube, the improvement comprising: said flow resistance comprising a single fixed resistance extending across the passageway of said flow tube and having a flow surface determining a basic resistance value $R_o$; and sinusoidally variable shutter means as resistance value varying means associated with said flow surface of said single fixed resistance for the periodic, substantially sinusoidal superposition of resistance variations $r$ onto said basic resistance value; said measuring means comprising flow measuring means connected to said flow tube and having first and second measurement passageways connected to the output of said flow measuring means, a first frequency filter in said first measurement passageway, a second frequency filter in said second measurement passageway, said first frequency filter having a frequency characteristic for ascertaining flow components $\dot{V}_o$ due to low frequency breathing, and the second frequency filter having a frequency characteristic for ascertaining flow components $\dot{v}$ due to the higher frequency resistance variations caused by said shutter means, and further comprising circuit means connected to the outputs of said first and second measurement passageways to provide the respiratory passageway resistance $R_{aw}$ from the lower and higher frequency flow components $\dot{V}_o$ and $\dot{v}$ obtained from said measurement passageways, and from the resistance values $R_o$ and $r$ in accordance with the relationship $$R_{aw} = R_o\left(\frac{r}{R_o} \cdot \frac{\dot{V}_o}{\dot{v}} - 1\right).$$

* * * * *